United States Patent
Wang et al.

(10) Patent No.: US 6,727,189 B2
(45) Date of Patent: Apr. 27, 2004

(54) METHOD FOR DETECTING METAL CONTAMINATION ON A SILICON CHIP BY IMPLANTING ARSENIC

(75) Inventors: Chuan-Yi Wang, Hsinchu (TW); Tsai-Sen Lin, Hsinchu (TW); Chon-Shin Jou, Hsinchu (TW); Chi-Ping Chung, Hsinchu (TW)

(73) Assignee: Mosel Vitelic, Inc., Hsinchu (TW)

( * ) Notice: Subject to any disclaimer, the term of this patent is extended or adjusted under 35 U.S.C. 154(b) by 68 days.

(21) Appl. No.: 10/105,507

(22) Filed: Mar. 26, 2002

(65) Prior Publication Data

US 2002/0137343 A1 Sep. 26, 2002

(30) Foreign Application Priority Data

Mar. 20, 2001 (TW) .................................. 90106430 A

(51) Int. Cl.⁷ ............................................. H01L 21/302
(52) U.S. Cl. ...................................... 438/745; 438/753
(58) Field of Search ............................ 438/745, 753, 438/755

(56) References Cited

U.S. PATENT DOCUMENTS

| 4,508,757 A | * | 4/1985 | Fabricius et al. ............ 438/444 |
| 4,577,396 A | * | 3/1986 | Yamamoto et al. ......... 438/582 |
| 5,520,769 A | * | 5/1996 | Barrett et al. ................. 438/14 |
| 5,801,416 A | * | 9/1998 | Choi et al. ................... 257/335 |
| 6,528,387 B1 | * | 3/2003 | Moriyasu et al. ........... 438/404 |

* cited by examiner

Primary Examiner—Kin-Chan Chen
(74) Attorney, Agent, or Firm—Townsend and Townsend and Crew LLP

(57) ABSTRACT

Embodiments of the present invention relate to implanting arsenic into a wafer to quickly detect if there is metal contamination, such as iron, aluminum, or manganese, on the wafer. In accordance with an aspect of the present invention, a method for detecting metal contamination of a silicon chip comprises implanting arsenic ions into the silicon chip, and etching the silicon chip with a chemical etching solution. The existence of any metal contamination is detected by observing occurrence of silicon pits on the silicon chip caused by reaction between the arsenic ions and the metal contamination and etching with the chemical etching solution.

15 Claims, 4 Drawing Sheets

METHOD FOR DETECTING METAL CONTAMINATION ON A SILICON CHIP BY IMPLANTING ARSENIC

CROSS-REFERENCES TO RELATED APPLICATIONS

This application claims priority from R.O.C. Patent Application No. 090106430, filed Mar. 20, 2001, the entire disclosure of which is incorporated herein by reference.

BACKGROUND OF THE INVENTION

The present invention relates to detecting metal on a silicon chip, more particularly to detecting iron, aluminum, and manganese contamination on wafers.

In semiconductor manufacturing, deposition of undesired metal particles or ions, e.g., iron, aluminum, or manganese, may occur on the surface of wafers. This deposition contaminates the wafers. Because most wafer manufacturing tools are made of aluminum, aluminum contamination may be dominant and will diminish the quality of wafers. Conventionally, these metal particles or ions are detected by the element analyzer. However, there are detection limits for the element analyzer and the metal contamination may be hard to trace because the content is so low.

Conventionally, two instruments can be used to detect metal contamination on silicon chips. The first instrument is the Second Ion Mass Spectrometer (SIMS). In the procedure for using SIMS to detect metal contamination on silicon chips, the silicon chip is cut into the proper size for a test sample. Detection of contamination on the test sample is then conducted. The disadvantage of this method is that contamination detection is limited in the test sample, and it is therefore time-consuming to complete the examination on the whole silicon chip.

Another procedure uses the Total X-Ray Reflection Fluorescence analyzer (TXRF). The silicon chip is placed into the TXRF and is scanned by X-ray. The disadvantage is that the operation takes one hour and only detects what kind the metal contamination is but not its location.

BRIEF SUMMARY OF THE INVENTION

Embodiments of the present invention relate to implanting arsenic into a wafer to quickly detect if there is metal contamination, such as iron, aluminum, or manganese, on the wafer.

In one embodiment, the first step is to implant the arsenic ion into a silicon chip, where the arsenic ion will react with iron, aluminum, or manganese ions on the chip to form arsenide, e.g., iron arsenate, aluminum arsenate, or manganese arsenate. The implanting of arsenic ions to form arsenide with iron, aluminum, or manganese ions will create silicon defects on the silicon chip. The second step is to etch the silicon chip with acidic chemical etching solution. Because the etching rate on the silicon defects area is faster than on the uncontaminated area, after etching, the silicon defects will form silicon pits which are easily observed by means of optical or electron microscopy.

The advantage of the present invention is its short detection time, easy confirmation, and subsequent determination of the location of any metal contamination.

In accordance with an aspect of the present invention, a method for detecting metal contamination of a silicon chip comprises implanting arsenic ions into the silicon chip, and etching the silicon chip with a chemical etching solution. The existence of any metal contamination is detected by observing occurrence of silicon pits on the silicon chip caused by reaction between the arsenic ions and the metal contamination and etching with the chemical etching solution.

In some embodiments, the metal contamination comprises at least one of Fe, Al, and Mn. The chemical etching solution comprises an acid etching solution. The acid etching solution may comprise HF and $HNO_3$. The acid etching solution may comprise at least one of $(Cu(NO_3)_2 \cdot 3H_2O)$, $CrO_3$, $CH_3COOH$, HF, $HNO_3$, and deionized water. The occurrence of silicon pits on the silicon chip is observed by microscopy.

In accordance with another aspect of the present invention, a method of detecting metal contamination on a silicon substrate comprises implanting arsenic ions into the silicon substrate, wherein the arsenic ions react with any metal contamination on the silicon substrate to form silicon defects. The silicon substrate is etched with a chemical etching solution to form silicon pits on locations of any silicon defects. The occurrence of any silicon pits on the locations is observed to detect metal contamination.

DETAILED DESCRIPTION OF THE INVENTION

Figure 1:
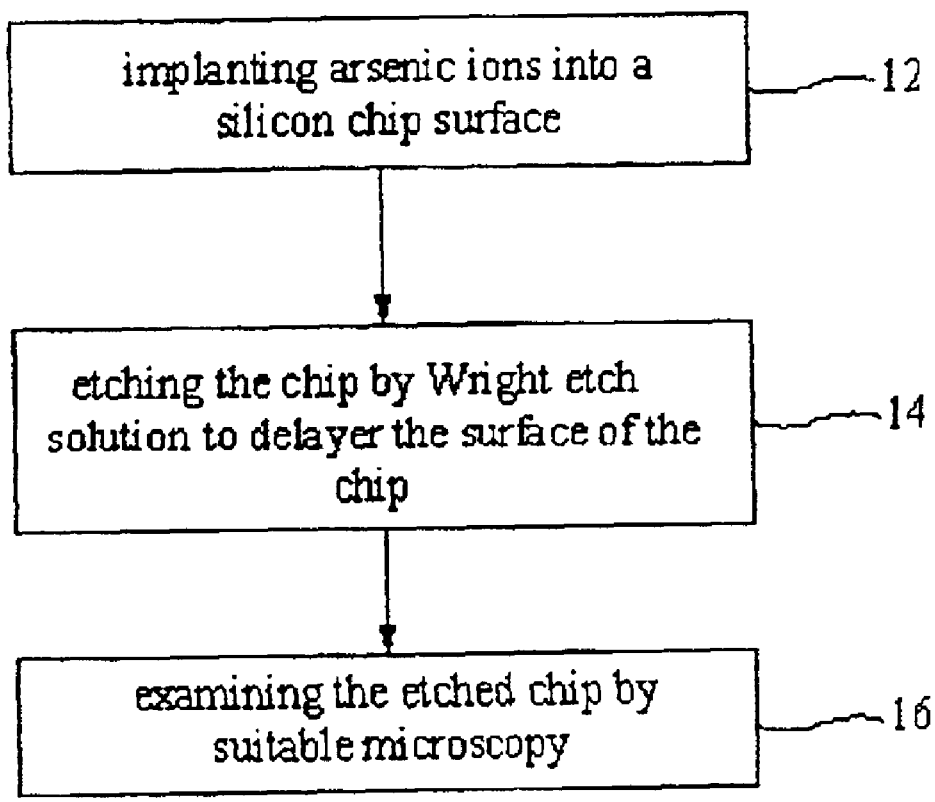
FIG. 1 is a flow chart illustrating a procedure for detecting metal on a silicon chip by implanting arsenic according to an embodiment of the present invention.

As shown in FIG. 1, the procedure for detecting metal on a silicon chip according to an embodiment of the invention includes implanting arsenic ions into a silicon chip surface (step 12). The chip is then etched to delaminate or delayer the surface of the chip (step 14). The etching can be performed using the Wright etch solution or other suitable solutions. The etched chip is examined to determine if metal contamination exists (step 16). The implanted arsenic ions will cause damage at locations on the chip with metal contamination. The examination can be conducted by, for instance, suitable microscopy.

Examples will be provided to illustrate in detail the procedure of the present invention. In the examples, the following equipment and parameters were used:

As/40 Kev/3E15

Chip Type: P-type Silicon wafer

Etching duration: 3 min.

Examining Instrument: HITACHI S4500 Electron Microscopy

Examining Magnification: 25K-30K

Figures 2A, 2B, 2C:
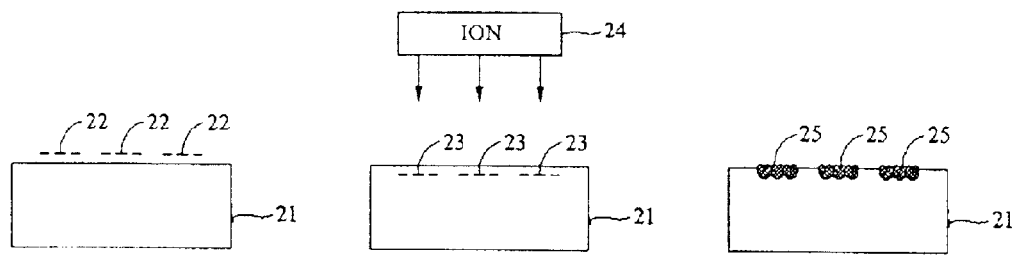
FIGS. 2a–2c are simplified diagrams illustrating the process flow of contamination detection by implanting arsenic into a silicon chip according to an embodiment of the present invention.

Referring to FIGS. 2a–2c, the procedure of one embodiment of the present invention is as follows:

Step 1: Implanting Arsenic Ions 24 Into the Surface of a Silicon Chip 21.

If there is any metal contamination 22, e.g., iron, aluminum, or manganese, on the chip 21 surface, the implanted arsenic ions form arsenides with these metal at sites where contamination is detected. The arsenides on the chip are submerged under the surface of the chip and form silicon defects. These silicon defects cause damage to the crystal lattice of the silicon nearby.

Step 2: Etching the chip by Wright Etch Solution to Delayer the Surface of the Chip.

The Wright etch solution formulation is as follows:

$Cu(NO_3)_2 \cdot 3H_2O$: 10 g $CrO_3$: 75 g $CH_3COOH$: 100%, 300 mL

HF: 49%, 300 mL $HNO_3$: 70%, 150 mL

Deionized Water: 400 mL

After etching, because the etching rate of the silicon defects area is faster than that of the uncontaminated area, the silicon defects are etched as silicon pits 25 on the silicon chip.

Step 3: Examining the Etched Chip by Suitable Microscopy.

The silicon pits are easily observed by optical or electron microscopy. If any silicon pits are observed by microscopy, the chip is contaminated by metal, e.g., iron, aluminum, or manganese. On the contrary, if there are no pits observed, the chip is uncontaminated.

When the implanted arsenic ions form arsenides with iron, aluminum, or manganese ions or particles, the crystal lattice near or at the metal contamination is damaged and therefore silicon defects form. It is easy to etch the chip with general acidic etching solution. The silicon pits appear because of the different etching rate between the uncontaminated silicon area and the areas of silicon defects. The acidic etching solution can be Wright etch solution, an acidic solution containing HF or $HNO_3$, or an acidic solution containing both HF and $HNO_3$, or the like.

Figure 3A:
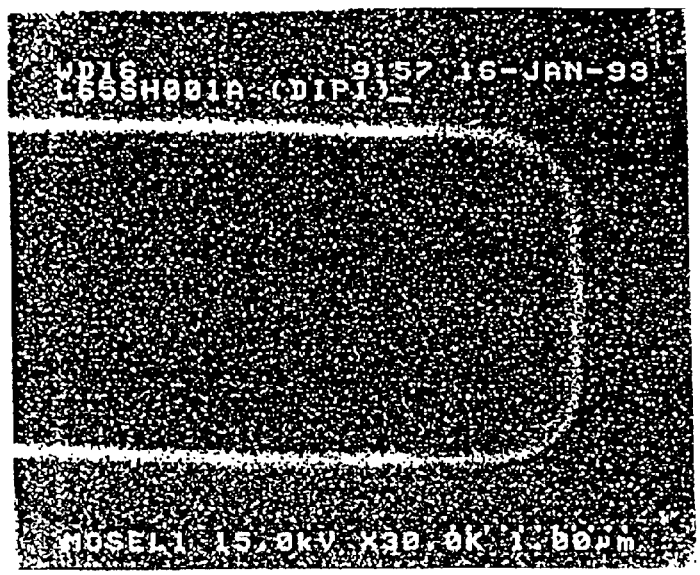
FIG. 3a is an electron microscopy image of an uncontaminated silicon chip which is treated with arsenic implanting and then etched by Wright etch solution.
Figure 3B:
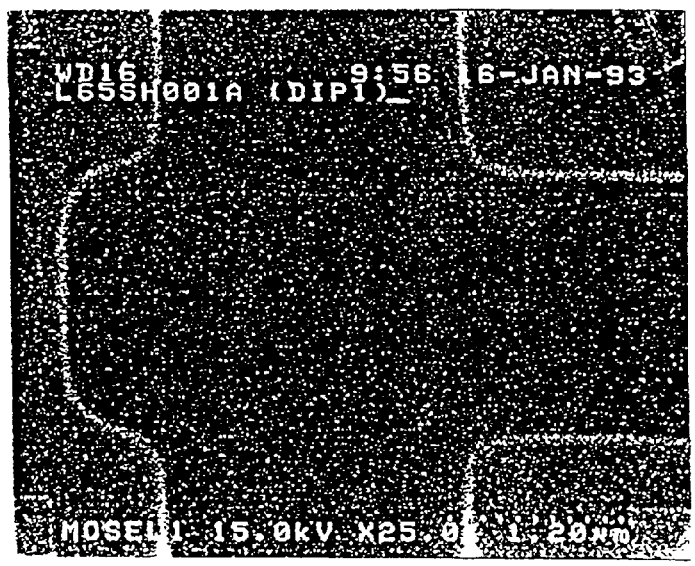
FIG. 3b is an electron microscopy image of an uncontaminated silicon chip which is not treated with arsenic implanting and is etched by Wright etch solution.

FIG. 3a is an electron microscopy image (HITACHI S4500, 30K) of an uncontaminated silicon chip treated with arsenic implanting and then etched by Wright etch solution. FIG. 3b is an electron microscopy image (HITACHI S4500, 25K) of an uncontaminated silicon chip untreated with arsenic implanting but etched by Wright etch solution. Comparing FIGS. 3a and 3b, when there is no metal contamination on the chips, there is no damage caused by arsenic implanting and Wright etch solution etching. The surface of both chips are even and intact.

Figure 4A:
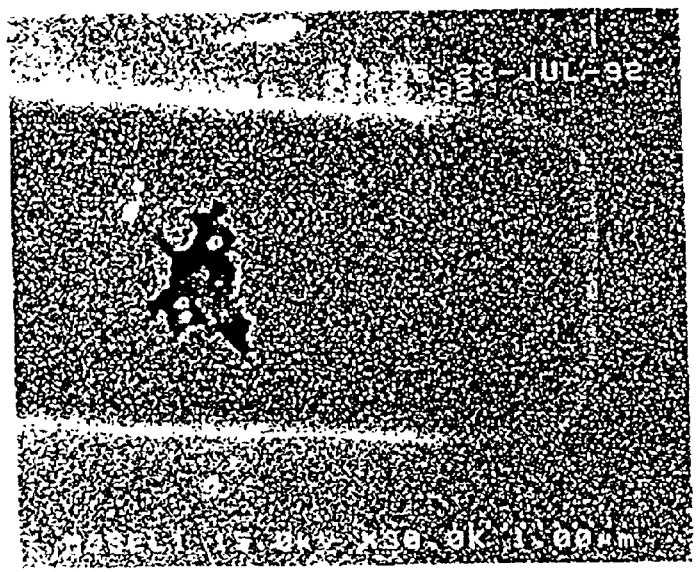
FIG. 4a is an electron microscopy image of a metal contaminated silicon chip which is treated with arsenic implanting and then etched by Wright etch solution.
Figure 4B:
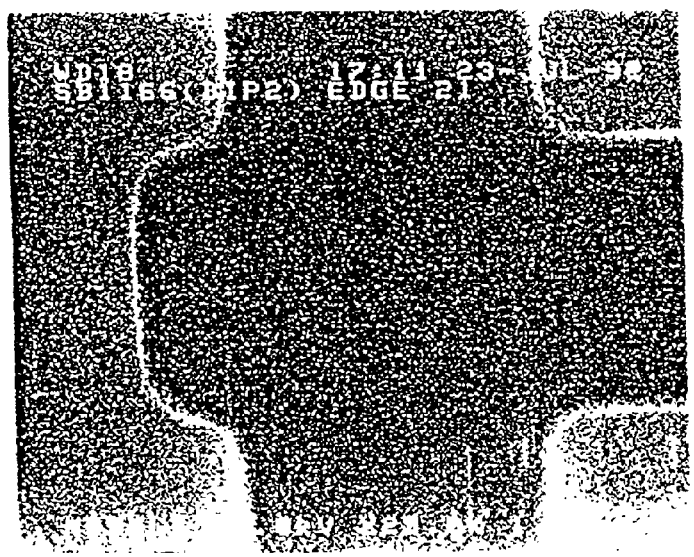
FIG. 4b is an electron microscopy image of a metal contaminated silicon chip which is not treated with arsenic implanting and is etched by Wright etch solution.

FIG. 4a is an electron microscopy image (HITACHI S4500, 30K) of a metal-contaminated silicon chip treated with arsenic implanting and then etched by Wright etch solution. FIG. 4b is an electron microscopy image (HITACHI S4500, 25K) of a metal-contaminated silicon chip untreated with arsenic implanting but etched by Wright etch solution. Comparing FIGS. 4a and 4b, when there is metal contamination on the chips, there will be damage caused by arsenic implanting (FIG. 4a) and Wright etch solution etching. Therefore the metal contamination on the chip is detected easily by microscopy. However, the chip in FIG. 4b still maintains an even and intact surface because the chip has not been implanted with arsenic.

The method of the present invention can easily trace or detect contaminated iron, aluminum, or manganese ions or particles on silicon chips even if the metals exist only in trace amounts. Another advantage of this invention is that it is easy to determine where the contaminants are located. Also, the method of the present invention is time-saving and efficient for metal contamination detection.

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

What is claimed is:

1. A method for detecting metal contamination of a silicon chip, the method comprising:

implanting arsenic ions into the silicon chip;

etching the silicon chip with a chemical etching solution; and detecting existence of any metal contamination by observing occurrence of silicon pits on the silicon chip caused by reaction between the arsenic ions and the metal contamination to form arsenide and etching with the chemical etching solution.

2. The method of claim 1 wherein the metal contamination comprises Fe.

3. The method of claim 1 wherein the metal contamination comprises Al.

4. The method of claim 1 wherein the metal contamination comprises Mn.

5. The method of claim 1 wherein the chemical etching solution comprises an acid etching solution.

6. The method of claim 5 wherein the acid etching solution comprises HF and $HNO_3$.

7. The method of claim 5 wherein the acid etching solution comprises at least one of $(Cu(NO_3)_2 \cdot 3H_2O)$, $CrO_3$, $CH_3COOH$, HF, $HNO_3$, and deionized water.

8. The method of claim 1 wherein the occurrence of silicon pits on the silicon chip is observed by microscopy.

9. A method of detecting metal contamination on a silicon substrate, the method comprising:

implanting arsenic ions into the silicon substrate, wherein the arsenic ions react with any metal contamination on the silicon substrate to produce arsenide and form silicon defects;

etching the silicon substrate with a chemical etching solution to reveal silicon pits on locations of any said silicon defects; and observing occurrence of any said silicon pits on said locations to detect metal contamination.

10. The method of claim 9 wherein the metal contamination comprises at least one of Fe, Al, and Mn.

11. The method of claim 9 wherein the metal contamination is selected from the group consisting of Fe, Al, and Mn.

12. The method of claim 9 wherein the chemical etching solution comprises an acid etching solution.

13. The method of claim 12 wherein the acid etching solution comprises HF and $HNO_3$.

14. The method of claim 12 wherein the acid etching solution comprises at least one of $(Cu(NO_3)_2 \cdot 3H_2O)$, $CrO_3$, $CH_3COOH$, HF, $HNO_3$, and deionized water.

15. The method of claim 9 wherein the occurrence of any said silicon pits on the silicon substrate is observed by microscopy.

* * * * *